United States Patent [19]

Fink

[11] Patent Number: 5,316,942
[45] Date of Patent: May 31, 1994

[54] PROCESS FOR THE PRODUCTION OF LOW-COST SOLUBLE HIGH-MOLECULAR WEIGHT COLLAGEN

[75] Inventor: David J. Fink, Shaker Heights, Ohio

[73] Assignee: Battelle Memorial Institute, Columbus, Ohio

[21] Appl. No.: 78,932

[22] Filed: Jun. 16, 1993

[51] Int. Cl.$^5$ .......................... C07K 3/12; C12P 21/00; C12N 9/99; A61K 37/12
[52] U.S. Cl. ................................ 435/273; 435/68.1; 435/71.1; 435/184; 435/213; 435/219; 435/212; 530/356
[58] Field of Search ...................... 435/71.1, 273, 213, 435/219, 212, 184, 68.1; 530/356

[56] References Cited

U.S. PATENT DOCUMENTS

| | | | |
|---|---|---|---|
| 2,637,321 | 9/1951 | Cresswell | 128/335.5 |
| 2,934,447 | 4/1960 | Highberger et al. | 106/155 |
| 3,223,551 | 12/1965 | Tu | 117/140 |
| 3,532,593 | 10/1970 | Young | 162/2 |
| 3,616,205 | 10/1971 | Ito et al. | 435/273 |
| 4,140,537 | 2/1979 | Luck et al. | 530/356 |
| 4,233,360 | 11/1980 | Luck et al. | 530/356 |
| 4,488,911 | 12/1984 | Luck et al. | 530/356 |
| 4,565,580 | 1/1986 | Miyata et al. | 530/356 |
| 4,655,980 | 4/1987 | Chu | 530/356 |
| 4,703,108 | 10/1987 | Silver et al. | 530/356 |
| 4,883,864 | 11/1989 | Scholz | 530/356 |
| 5,137,875 | 8/1992 | Tsunegaga et al. | 530/356 |

OTHER PUBLICATIONS

The Preparation and Properties of Solubilized Collagens; N. T. Crosby et al.; J. Soc. Lea. Trades Chemists; 46; 1962; pp. 152–161.
Comminuted Collagen: Estimated Costs of Commercial Production; V. A. Turkot et al.; Food Technology; Apr. 1978; pp. 48–57.
The Use of Collagen Dispersions During the Manufacturing of Paper; J. Tkac et al.; Kozarstvi 30; 11; 1980; pp. 324–326.

*Primary Examiner*—Herbert J. Lilling
*Attorney, Agent, or Firm*—Klaus H. Wiesmann

[57] ABSTRACT

The invention includes a method that produces a low cost aqueous solution of high molecular weight solubilized collagen by the steps of: (a) providing an aqueous ground slurry of insoluble collagen; (b) adjusting the water or solid content of the wet ground slurry whereby the insoluble collagen is at a concentration that promotes substantially maximum solubilized collagen concentration and molecular weight in a final product; (c) adjusting the pH of the slurry from Step b to obtain activity for a proteolytic enzyme added in Step d; (d) adding the proteolytic enzyme to the pH adjusted slurry and reacting at a temperature, T, and for a time, t, effective for forming high molecualr weight solubilized collagen from the insoluble collagen particles; (e) controlling the reaction conditions for obtaining a high concentration of soluble collagen and a high molecular weight of the solubilized collagen by simultaneously measuring the concentration of solubilized collagen and the molecular weight of the solubilized collagen, whereby the reaction is complete when the molecular weight and the concentration are substantially maximized; and (f) withdrawing the aqueous solution of high molecular weight solubilized collagen as product. Proteolytic enzyme recycle steps are disclosed that can be used to further reduce costs.

14 Claims, 4 Drawing Sheets

PROCESS FOR THE PRODUCTION OF LOW-COST SOLUBLE HIGH-MOLECULAR WEIGHT COLLAGEN

FIELD OF THE INVENTION

The invention involves the low-cost production of solubilized collagen having a high molecular weight. Solubilized collagen with high molecular weight is useful in the production of high strength paper, or as a binder for cellulosic products.

BACKGROUND OF THE INVENTION

The processing of animal hides to produce leather is an ancient art, and today it is a very mature industry. Excellent references to the chemistry of leather manufacture by McLauglin, G. D., et al, *The Chemistry of Leather Manufacture*, Reinhold Publishing Corp, N.Y. (1945), and collagen reactivity by Gustavson, K. H., *The Chemistry and Reactivity of Collagen*, Academic Press Inc., N.Y. (1956), date from the 1940's and 1950's, and are still basic descriptions of the art practiced today. The name "collagen" is derived from the Greek word for glue, as is the term "colloid" which means "gluelike" in Greek.

Skin is composed of four distinct layers, which are, proceeding from outside-in: (1) a thin outer layer of epithelium termed the "epidermis", which is rich in the protein keratin, not collagen; (2) a dense collagen-rich layer, termed the "dermal" or "grain" layer, also called in the older literature the "thermostat" layer; (3) a thicker layer of less-dense, collagen-rich connective tissues, termed the "corium" layer; and (4) an inner layer of "subcutaneous tissue", known to the tanner as "flesh", by which the skin is attached to the underlying tissue.

Although hides may merely be "cured" in salt and/or other biocidal solutions to stop microbial degradation, many hides that are intended for use in leather manufacture are "limed", that is, soaked in a saturated solution of hydrated lime (calcium hydroxide) and water. The liming process initiates the loosening of the epidermis and the subcutaneous layer, and is the first step in the dehairing process. After liming is complete, the hair, epidermis, and any residual flesh, fat and surface muscles are removed by mechanical scraping, and the dermal layer is mechanically cut, along with enough of the corium layer to give the final leather its required thickness, from the remaining inner corium layer.

In leather-making the primary interest is on the dense collagen-rich dermal layer, which is about 25% of the thickness of the corium layer. During the process of leather-making, the dermal tissue receives separate chemical and tanning treatments to stabilize the collagen structure.

The residual portion of the corium layer that is separated from the dermal layer is termed the "limed split" and is a by-product waste of the leather manufacturing process. It is these limed splits that become, for example, the collagen-rich feedstock for sausage casing production, and that have been used as the source of collagen for the examples herein.

During the liming process, the skin imbibes and binds water, and becomes highly swollen; in the process it acquires a very alkaline pH of about 12.5. The chemistry of the liming process is quite well understood. Prior to further leather processing, and in the collagen production process considered here, the skins must be "delimed" by soaking in acid or salt solutions.

Four U.S. Pat. Nos. (4,140,537, 4,233,360, 4,488,911, 4,655,980) all assigned to Collagen Corporation, describe enzymatic methods, including pepsin hydrolysis, for solubilizing collagen to produce a "non-immunogenic" soluble collagen, which is then converted to other forms for use as medical implants. In these patents, the initial soluble product is relatively low (for collagen) molecular weight aggregates (about 300,000 daltons); the objective is to remove all of the "telopeptides" which are found at the end of these chains. Higher molecular weight aggregates would not have the telopeptides completely removed, and would be more "immunogenic" by their standards.

A 1970 U.S. Pat. No. (3,532,593) describes a method for making collagen for use in papermaking. It describes a mechanical method for isolating preexisting gelled collagen fibers, not an enzymatic method for solubilizing the collagen as in the present invention. This patent describes a method for adjusting the pH of mechanically gelled collagen to promote flotation of fat and for skimming the floating fat from the collagen. The patent also refers to the partial "gelatinizing" of the collagen by heating to improve the bonding properties of the additive, although the primary objective is to produce a fibrous product.

SUMMARY OF THE INVENTION

A first embodiment of the invention is a method that typically produces an aqueous solution of high molecular weight solubilized collagen by the steps of: (a) providing an aqueous ground slurry of insoluble collagen; (b) adjusting the water or solid content of the wet ground slurry whereby the insoluble collagen is at a concentration that promotes substantially maximum solubilized collagen concentration and molecular weight in a final product; (c) adjusting the pH of the slurry from Step b to obtain activity for a proteolytic enzyme added in Step d; (d) adding the proteolytic enzyme to the pH adjusted slurry and reacting at a temperature, T, and for a time, t, effective for forming high molecular weight solubilized collagen from the insoluble collagen particles; (e) controlling the reaction conditions for obtaining a high concentration of soluble collagen and a high molecular weight of the solubilized collagen by simultaneously measuring the concentration of solubilized collagen and the molecular weight of the solubilized collagen, whereby the reaction is complete when the molecular weight and the concentration are substantially maximized; and (f) withdrawing the aqueous solution of high molecular weight solubilized collagen as product. The reaction is typically stopped by adjusting the pH to that where the proteolytic enzyme is substantially inactive; and/or reducing the temperature to that where the proteolytic enzyme is substantially inactive. The reaction is typically controlled by measuring solution viscosity at two different shear rates whereby the reaction is complete when a ratio of (viscosity at low shear)/(viscosity at high shear) is substantially maximized. The viscosity ratio is preferably at least 75% of maximum. Preferably at least 80 wt % of the insoluble collagen is converted to soluble collagen and the number average molecular weight is above 300,000 daltons or more preferably above 600,000 daltons; and most preferably at least 90 wt % of the insoluble collagen is converted to soluble collagen and the number average molecular weight is above 1,000,000 daltons. In a preferred embodiment the solids content of the wet ground slurry is adjusted to a concentration of about 0.1 to about 1.0 wt %, and the temperature, T, is about 5° C. to about 35° C., while more preferably the temperature, T, is between about 15° C. to about 30° C. In other typical embodiments in Step b, the solids concentration is between about 0.3 to 0.35 wt %; and in Step e. the reaction is controlled at a temperature of about 20 to about 30° C., and for time of 24 to 48 hours. Since many different sources of collagen can be used it is difficult to enumerate all of the proteolytic enzymes that can be used with the process of the invention, however, these can easily be selected by those skilled in the art. Some examples of proteolytic enzymes include those selected from the group consisting of porcine mucosal pepsin, bromelain, chymopapain, chymotrypsin, collagenase, ficin, papain, peptidase, proteinase A, proteinase K, trypsin, and similar enzymes or combinations of such enzymes. Typically the pH is adjusted to between about 1.5 to about 3.0 and the temperature to between about 26° to about 28° C., when porcine mucosal pepsin is selected.

Another typical embodiment of the method for producing an aqueous solution of high molecular weight solubilized collagen includes the steps of: (a) providing an aqueous ground slurry of insoluble collagen; (b) adjusting the water or solid content of the wet ground slurry whereby the insoluble collagen is at a concentration that promotes substantially maximum solubilized collagen concentration and molecular weight in a final product; (c) adjusting the pH of the slurry from Step b to obtain activity for a proteolytic enzyme added in Step d; (d) adding the proteolytic enzyme to the pH adjusted slurry and reacting at a temperature, T, and for a time, t, effective for forming a solution of high molecular weight solubilized collagen from the insoluble collagen particles; (e) controlling the reaction to obtain a high concentration of soluble collagen and a high molecular weight of the solubilized collagen by simultaneously measuring the concentration of solubilized collagen and the molecular weight of the solubilized collagen, whereby the reaction is complete when the molecular weight and the concentration are substantially maximized; (f) adding additional water and insoluble collagen to the solution containing high molecular weight solubilized collagen in Step d and mixing; (g) separating at least some of the solution containing high molecular weight solubilized collagen from the insoluble collagen and returning the insoluble collagen to Step b, whereby at least a portion of the proteolytic enzyme is recycled, and the separated solution containing high molecular weight solubilized collagen is withdrawn as product. The embodiment can include repeating Steps f and g one or more times. Alternatively, the recycling of proteolytic enzyme can be generally performed by extraction and recycle to earlier process steps by other methods generally known in the art. The reaction is typically stopped by adjusting the pH to that where the proteolytic enzyme is substantially inactive; and/or reducing the temperature to that where the proteolytic enzyme is substantially inactive. The reaction is typically controlled by measuring solution viscosity at two different shear rates whereby the reaction is complete when a ratio of (viscosity at low shear)/(viscosity at high shear) is substantially maximized. The viscosity ratio is preferably at least 75% of maximum. Preferably at least 80 wt % of the insoluble collagen is converted to soluble collagen and the number average molecular weight is above 300,000 daltons or more preferably above 600,000 daltons; and most preferably at least 90 wt % of the insoluble collagen is converted to soluble collagen and the number average molecular weight is above 1,000,000 daltons. In a preferred embodiment the solids content of the wet ground slurry is adjusted to a concentration of about 0.1 to about 1.0 wt %, and the temperature, T, is about 5° C. to about 35° C., while more preferably the temperature, T, is between about 15° C. to about 30° C. In other typical embodiments in Step b, the solids concentration is between about 0.3 to 0.35 wt %; and in Step e. the reaction is controlled at a temperature of about 20° to about 30° C., and for time of 24 to 48 hours. Since many different sources of collagen can be used it is difficult to enumerate all of the proteolytic enzymes that can be used with the process of the invention, however, these can easily be selected by those skilled in the art. Some examples of proteolytic enzymes include those selected from the group consisting of porcine mucosal pepsin, bromelain, chymopapain, chymotrypsin, collagenase, ficin, papain, peptidase, proteinase A, proteinase K, trypsin, and similar enzymes or combinations of such enzymes. Typically the pH is adjusted to between about 1.5 to about 3.0 and the temperature to between about 26° to about 28° C., when porcine mucosal pepsin is selected.

A yet further embodiment typically includes a method for producing an aqueous solution of high molecular weight solubilized collagen using the steps of: (a) providing an aqueous ground slurry of insoluble collagen; (b) adjusting the water or solid content of the wet ground slurry so that the solids are adjusted to a concentration of about 0.1 to about 1.0 wt %; (c) adjusting the pH of the slurry from Step b to obtain activity for a proteolytic enzyme added in Step d; (d) adding the proteolytic enzyme to the pH adjusted slurry and reacting at a temperature, between about 5° C. to about 35° C., and for a time, t, effective for forming high molecular weight solubilized collagen from the insoluble collagen particles; (e) controlling the reaction conditions for obtaining a high concentration of soluble collagen and a high molecular weight of the solubilized collagen by simultaneously measuring solution viscosity at two different shear rates whereby the reaction is complete when a ratio of (viscosity at low shear) divided by (viscosity at high shear) is substantially maximized; and (f) withdrawing the aqueous solution of high molecular weight solubilized collagen as product.

Feed material for the process can typically come from a variety of sources as long as the feed is relatively clean and has collagen containing material of relatively small particle size. One typical method for preparing the feed material of a wet ground slurry of insoluble collagen from animal tissues includes the steps: (a) providing soft animal tissues containing collagen; (b) cleaning the collagen containing tissues to remove hair, fat, carbohydrates, and other contaminants; (c) cutting the cleaned collagen containing tissues into small pieces; (d) mixing the small pieces with water to obtain a slurry; (e) adjusting the pH of the slurry substantially near the isoelectric point of collagen from the tissues; (f) wet grinding the resulting pH adjusted slurry to obtain a slurry of insoluble collagen. The pH of this method is typically about 3 to about 7.

The invention further encompasses the unique aqueous solutions of high molecular weight solubilized collagen produced by the above methods.

DETAILED DESCRIPTION OF THE INVENTION

It was recognized that a high-molecular-weight soluble collagen material, added to the pulp prior to the papermaking process (i.e, mixed with the pulp fibers in the machine chest), resulted in a significant increase in strength of the paper-collagen composite. There is no current large-scale use or commercial source for a collagen solution of this type. Small-scale applications for soluble collagen exist in the food, cosmetic and pharmaceutical industries, for which the products are much higher priced than will be economically acceptable in the subject paper application.

Therefore, the advantages of the invention are in: (1) minimizing the cost of preparing soluble collagen by processing directly from ground skin material to the maximum amount of soluble macromolecules; and (2) at the same time, maximizing soluble collagen material and the molecular weight of the soluble collagen material in order to enhance the binding effect to the pulp fibers, thereby maximizing the resulting tensile strength and/or other mechanical properties of the paper product.

Beef skin was selected as the collagen source in the examples described here because collagen preparation methods from skin have been widely reported, and the material is a high volume by-product of the major industries of beef production and leather manufacture; however, it is expected that collagen obtained from other sources (e.g. tendon) will work in the process also.

Collagen solubilization of skin has been accomplished by an enzymatic hydrolysis process with an animal stomach enzyme (pepsin) without any other purification steps. The process results in nearly complete solubilization of ground hide preparations in 20–30 hours at room temperature in acidic solutions. Other (untested) enzymes may yield faster or cheaper conversion of collagen-containing tissues, and the process has not necessarily been optimized to minimize enzyme requirements and production time. To date, the process has been scaled to produce approximately 500 gallons of 0.3–0.4% collagen solution, and it has been demonstrated to be relatively easy to control.

EXAMPLES

The following examples, illustrative of the novel compositions and the novel methods of preparing them, are given without any intention that the invention be limited thereto.

Materials

The pepsin used was a crude (relatively unpurified) powder from pig stomach mucosa (Cat. No. P7125) purchased from Sigma Chemical Company, St. Louis, Mo. Lot #070H0437 of this product, used in the examples, contains approximately 15% protein (by UV), with an activity of 91 pepsin units/mg solids and 620 units/mg protein. Residual solids in the preparation appear to be a combination of precipitation salts, buffer salts and/or carbohydrates. Crystallized pepsin has a maximum specific activity of about 3500 units/mg protein.

The collagen slurry used herein for all pepsin reactions was prepared from ground limed-splits of bovine skin. The collagen was supplied by Teepak's Sandy Run Plant, Columbia, S.C. Typical analyses for the material of Example 6 are pH=6.4; solids content=15.67%; gelatin content=2.62%; fat content=2.1%. A 1974 USDA report by Komanowsky, M., et al, "Production of Comminuted Collagen for Novel Applications", *J. American Leather Chem. Assoc.*, 6, 410–422 (1974), describes techniques for pre-slicing, acidifying and wet-grinding of limed splits to produce five "comminuted" (ground) collagen products, classified by extent of grinding and the resulting particle size and texture. A subsequent 1978 paper by Turkot, et al, "Comminuted Collagen: Estimated Costs of Commercial Production", *Food Tech.*, 48–57 (April, 1978), presents an economic analysis of the production costs for these same five products. The output from this plant closely approximates the ground limed-split material used as a source for collagen in the examples herein.

Control—A soluble control collagen solution ("BA-1"), used as a control solution in the examples, was supplied as the soluble skin product, Secolan BA-1, by Kensey Nash Biomaterials, Exton, Pa. The solution is typically a white milky color; pH=3.1-3.3; total solids=1% ±0.2%; active collagen >0.67% (nominally 1% in the examples). This product is sometimes found to be slightly gelled upon receipt. However, based on the pattern observed after electrophoretic analysis, it is believed that the BA-1 is produced by an acid-extraction process, not by an enzymatic reaction as practiced in the present invention.

It was found that the solubilization of collagen-containing solids can be effectively monitored by periodic measurement of the solution viscosity. Fluid viscosities can be conveniently measured by a variety of relatively simple methods, such as the Brookfield Model #RVT Viscometer (#3 Spindle) used with the examples. In this Brookfield system, the force exerted by a fluid upon a disk, which is rotated at constant rotational speed in the fluid, is used to estimate the fluid viscosity. In the collagen solutions described herein, the fluid viscosity will be strongly dependent on the concentration of dissolved collagen, the molecular weight distribution of the soluble collagen and the fluid temperature, and, to a lesser extent, fluid pH and ionic strength.

When the viscosity is independent of the applied force (shear), then the fluid is said to be "Newtonian". For solutions of many macromolecules, including the rod-like collagen molecules considered here, the solution viscosity is very dependent on the force applied to the liquid, and the liquid is said to be "non-Newtonian". When the dissolved macromolecules are highly elongated, and the shear rate (proportional to the rotational speed) is sufficiently high, the molecules tend to orient with the streamlines of the fluid and their effect on the fluid velocity tends to decrease in a manner that is strongly dependent on the shear rate.

Figure 1A:
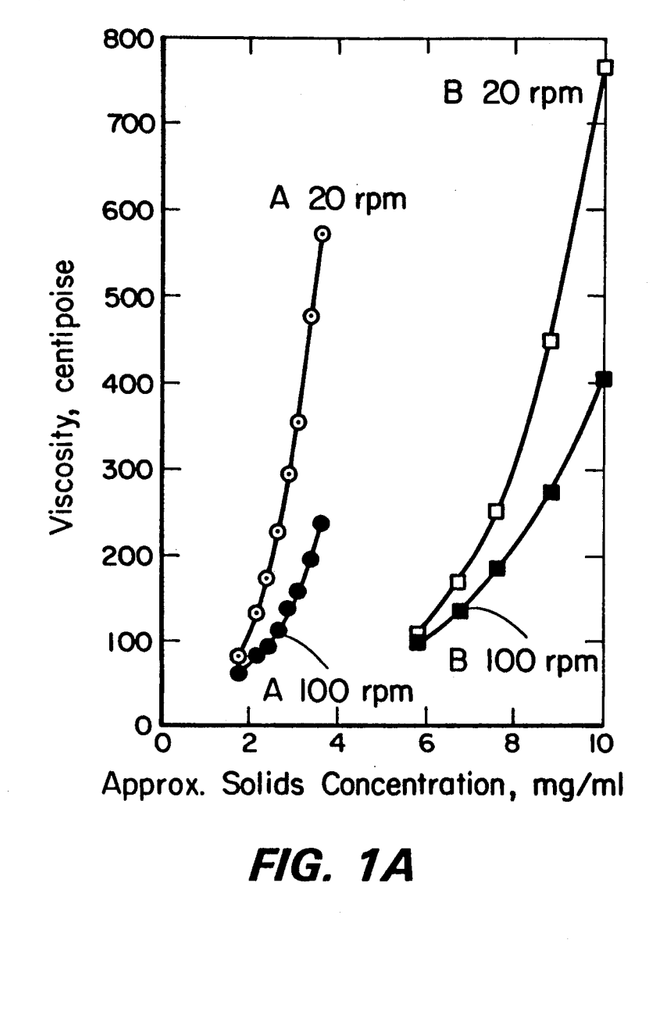
FIG. 1A is a plot showing the non-Newtonian behavior of the collagen solutions. Viscosity of diluted solutions of high molecular weight solubilized collagen of the invention (A) and BA-1 collagen solutions (B) at two shear rates (20 and 100 rpm).

The non-Newtonian behavior of collagen solutions is demonstrated in the experiments summarized in FIG. 1A, in which the viscosity of preparations of solubilized collagen and BA-1 were determined at room temperature as the solutions were progressively diluted with distilled water. Some uncorrected increase in solution pH may have occurred in this experiment as the samples were diluted; however, the trend for the data is valid.

For each solution, the viscosity was determined at two rotational speeds, 20 and 100 rpm. The open circles (-⊙-)

and filled circles (-●-)

represent data for solubilized collagen of the invention at 20 rpm and at 100 rpm, respectively. The open squares (-□-)

and the filled squares (-■-)

represent the data for the BA-1 collagen control at 20 rpm and 100 rpm respectively. Both solutions were more viscous at the lower rotational rate, as expected. The viscosities of the collagen produced in the examples and BA-1 preparations were substantially different, with the produced collagen solution having a much higher viscosity at lower collagen concentrations and a steeper slope. These effects appear to be primarily due to the difference in the average molecular weights of the collagen molecules in the two solutions, with the collagen solution of the invention having the larger average molecular size. The comparison shows that the method of the invention was successful in making a higher viscosity collagen material at a lower concentration thus showing the molecular weight was higher.

Figure 1B:
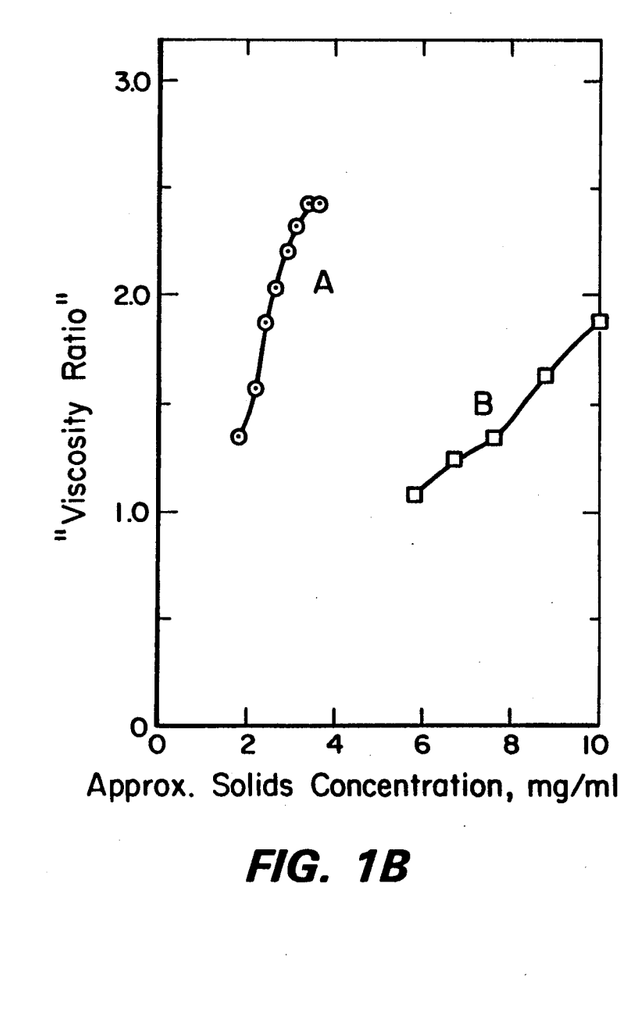
FIG. 1B is a plot showing the ratio of the viscosity determined at 20 rpm to the viscosity at 100 rpm, termed here the "viscosity ratio". The data is calculated from the data in FIG. 1A for both the high molecular weight solubilized collagen (A) or the BA-1 collagen solutions (B).

The ratio of the viscosity determined at 20 rpm to the viscosity at 100 rpm, termed here the "viscosity ratio", is a convenient measure of this non-Newtonian, molecular-weight-dependent effect. This is illustrated in FIG. 1B, in which the viscosity ratio is higher for collagen solutions of the invention than for BA-1. In FIG. 1B the open circles (-⊙-)

represent data from the solubilized collagen of the invention and the open squares (-□-)

represent data from the BA-1 collagen solution. The viscosity ratio is used herein is a measure of the "degree of conversion" of solid collagen materials to soluble collagen molecules and also a measure of molecular weight, where higher values of the viscosity ratio will correlate with the desired higher average molecular weights of the dissolved collagen. In FIG. 1B it is important to note that since the material is being diluted, an increase in viscosity ratio is measuring the increase in concentration of soluble collagen since the molecular weight of the material remains the same. In tests of the examples below, changes in the viscosity ratio will be measuring changes in concentration as well as molecular weight.

Analysis of collagen composition was routinely performed by SDS polyacrylamide gel electrophoresis (PAGE) that used a 3% stacking gel; 6% running gel, following denaturation by boiling with B-mercaptoethanol. Some irreversible precipitation occurs during the denaturation process. Gels were stained by Coomassie Blue dye and destained in staining buffer only.

PAGE demonstrates (results not shown here) that BA-1 solutions contain predominately tropocollagen monomer (300,000 daltons) aggregates. Collagen solutions produced by the present process that had viscosity ratios higher than 2.0 had much broader molecular weight distributions, with some components smaller than alpha chains but with predominately higher molecular weight components that appear to exist in solution in aggregates having molecular weights higher than 1,000,000 daltons.

In the examples below, it was determined that ground limed splits of beef hide can be nearly completely solubilized when they are subjected to pepsin hydrolysis at pH in the range of 2.0–2.2. Batch reaction times are typically 20–30 hours at room temperature (22°–26° C.). The maximum concentration of soluble collagen produced in this process is approximately 0.30–0.40% (3–4 mg dissolved collagen/ml). The process has been demonstrated at up to 2.0 liter-scale and, using essentially the same recipe, at approximately 500-gal scale, as discussed below.

EXAMPLE 1

Approximately 15 g of wet Teepak collagen solids were suspended by magnetic stirrer in 750 ml of Columbus, Ohio tap water at room temperature. The solution pH was adjusted to 2.1 with concentrated hydrochloric acid (HCl)—approximately 65–70 drops. Crude pepsin powder (0.38 g) was then added with stirring into the collagen suspension to initiate the reaction. The suspension was stirred overnight, during which heating of the solution to 26°–27° C. or higher sometimes occurred due to conduction from the stirrer plate. The viscosity of the solution was measured (20 & 100 rpm) periodically during the second day of the reaction until a maximum in the viscosity ratio was achieved, at which time the solution can be stabilized by increasing the pH to 3.0–3.5 and/or by placing the solution in the refrigerator. Increasing the pH above 4.0 may initiate irreversible gelation of the collagen solution.

Figure 2:
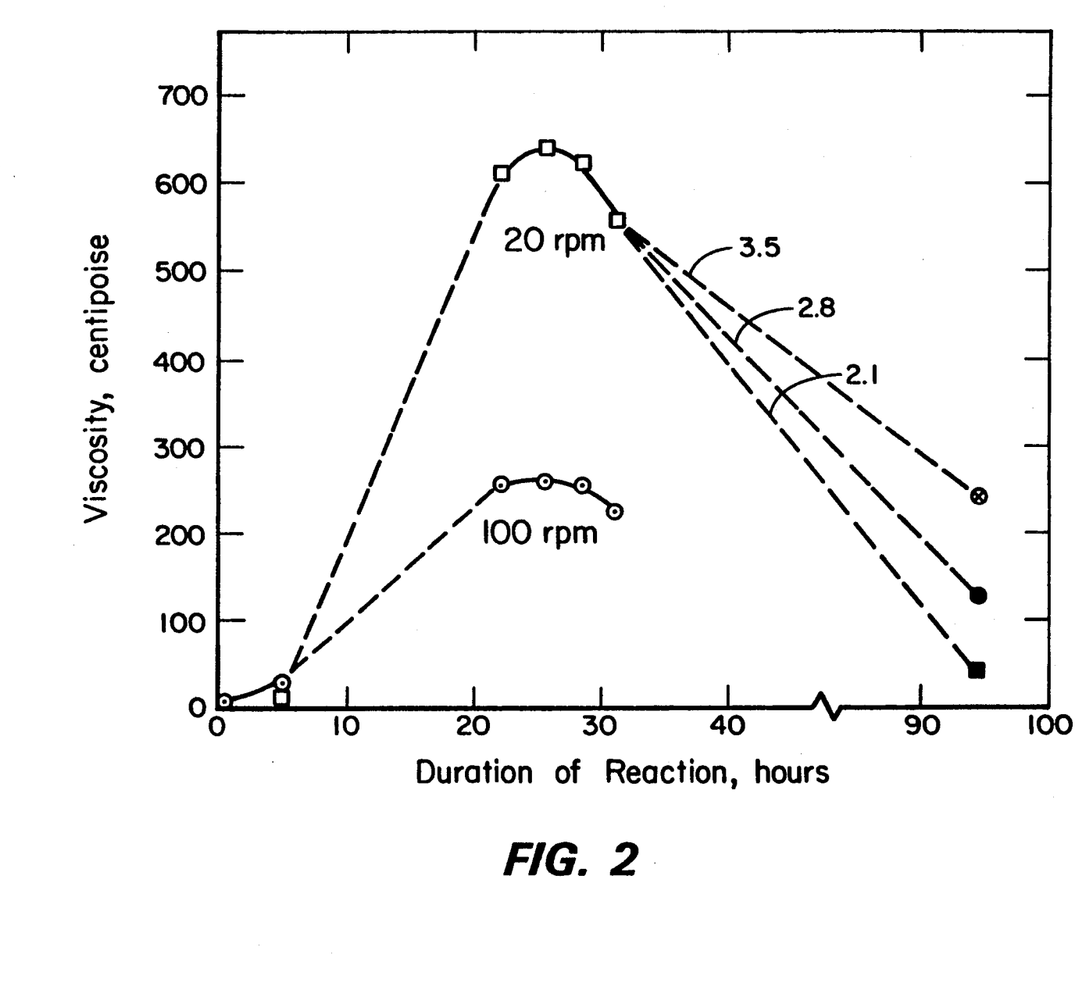
FIG. 2 is a plot of the data for Example 1 showing the viscosity at 20 rpm and 100 rpm.

Results for Example 1 are plotted in FIG. 2. FIG. 2 shows a plot of viscosity, (in centipoise) as a function of time reaction (in hours). Viscosity measurements were taken at 20 rpm (squares) and 100 rpm (circles). After completion of the reaction at pH 2.1, three samples were taken and the pH adjusted to 2.1, (-■-)

2.8, (-●-)

, and 3.5 (-⊗-)

Viscosity tests at 20 rpm taken several days later confirmed that the samples at pH=3.5 were indeed more stable and retained more of the original viscosity than those at pH=2.1.

EXAMPLE 2

Hydrolysis of Teepak collagen at temperatures between 30°–35° C. was investigated in a series of approximately 10 experiments to determine the potential for minimizing pepsin usage in the solubilization process. Typically, enzyme-catalyzed reaction rates will double with every 5°–10° C. increase in temperature. In these experiments, a 4-liter stainless steel beaker was wrapped with heating tape, then insulated with asbestos tape.

The solution temperature was controlled by a Variac in line with the heating tape to about ±1°–2° C. The process above was scaled to 2 liters of reaction volume, and a range of lower pepsin concentrations and heating profiles was investigated. In nearly all cases, complete solubilization of the Teepak solids was accomplished in 10–15 hours, and in no case was substantial viscosity developed in the solubilized product.

Typical of the ten experiments is the following: 2 liters of water were added to a beaker, to which was added 40 g of Teepak collagen, then the pH was adjusted to 2.13 with concentrated HCl, and finally 1.0 g crude pepsin was added. Initially the bath temperature was 30.0° C., about 2.5 hours later the temperature was 33° C. and the viscosity at 100 rpm was 19 cps, and about 5.5 hours later the temperature was 36.5° C. with a viscosity of 8 cps. The sample was completely solubilized in less than 8 hours at 33°–36° C. with no increase in viscosity indicating the production of a higher molecular weight material. These experiments demonstrate that it is expected to be more difficult to conserve pepsin in this process by operating at higher reaction temperatures, even early during the hydrolysis process. The maximum feasible temperature for accumulating this particular large molecular weight collagen appears to be about 30° C.

EXAMPLE 3

Figure 3:
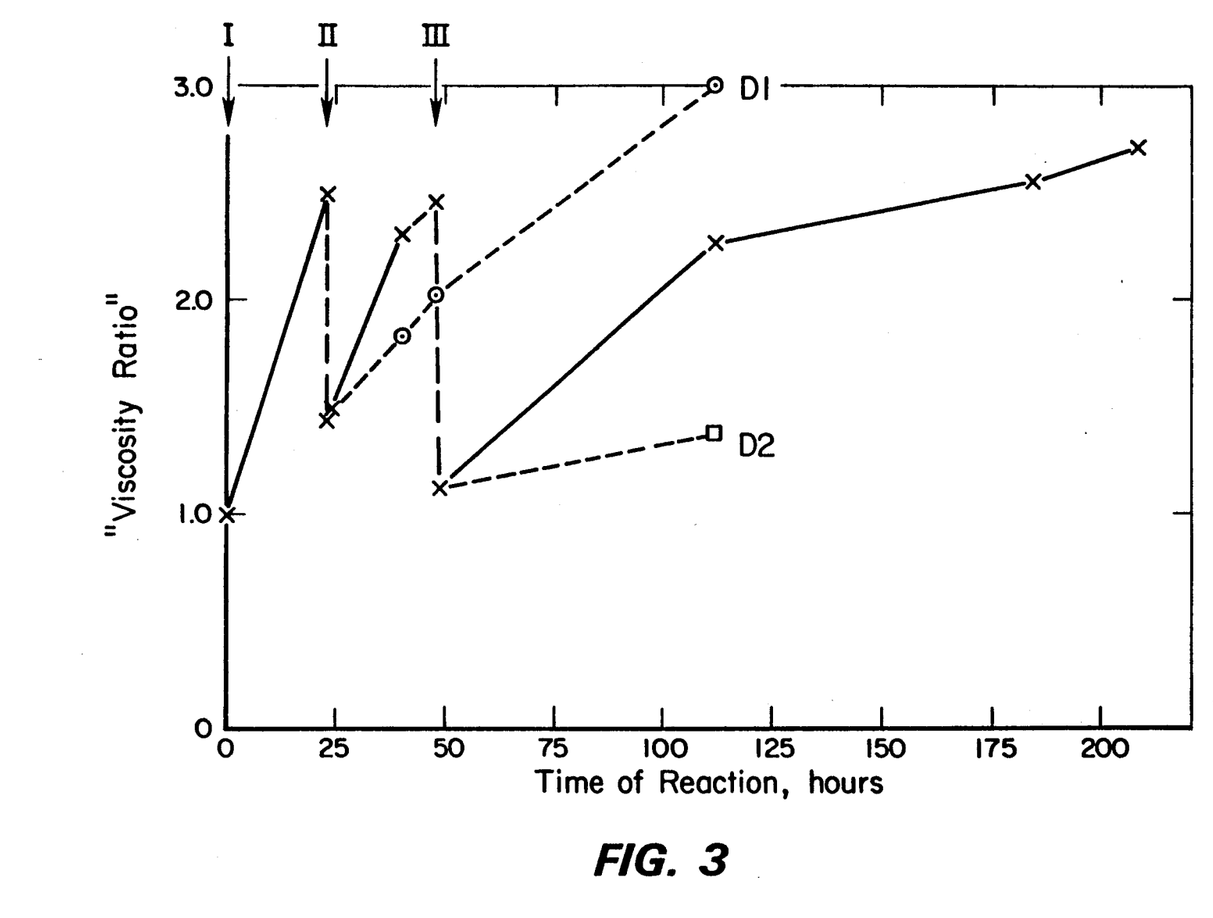
FIG. 3 is a plot of a small-scale batch collagen solubilizing reaction demonstrating the pepsin recycle of Example 3.

Another approach for minimizing pepsin usage in the process is illustrated by the experiment summarized in FIG. 3. In this experiment, the recipe above (750 ml Columbus, Ohio tap water, 15.5 g teepak collagen, 0.38 g pepsin, pH=2.1) was mixed on Day 0 to initiate the reaction in a 2-liter flask at room temperature (Roman numeral I). After approximately 1 day, an additional 750 ml of water and another charge of Teepak collagen solids (16.1 g) were added, but no additional pepsin was added to the reactor (Roman numeral II). The flask was stirred for about 5 minutes to mix the contents and the pH was readjusted with 30 drops of concentrated HCl, then the stirrer was turned off and the solids were permitted to settle out. After approximately 30 minutes, 750 ml of supernatant, "Day 1" supernatant (D1), was decanted into another flask, and stirring of both flasks was resumed. The Day 1 Supernatant contained some fine collagen particles, but it contained a much lower suspended solids load than the bottom fraction. The same process of dilution (755 ml water), collagen solids addition (15.2 g Teepak collagen), pH adjustment with 30 drops concentrated HCl (Roman numeral III), and supernatant decanting of "Day 2" supernatant (D2) was repeated in the first flask after approximately 2 days of reaction.

The progression of the hydrolysis reaction is illustrated by the solid lines (-x-) in FIG. 3. The circles ( -⊙- ) show a plot of the progression hydrolysis reaction of the Day 1 supernatant while the squares (-☐-) show a plot of the Day 2 supernatant. In this example three typical charges of Teepak collagen were hydrolyzed by a single charge of pepsin, although the rate of hydrolysis appears to be decreasing with each cycle. Because the viscosity ratios of both the Day 1 and Day 2 supernatants appeared to increase after they were decanted from the main reactor, it was apparent that some pepsin and insoluble collagen was transported along with the supernatant. However, it appears that the pepsin has a higher affinity for solid collagen particles than for soluble collagen, thus most of the enzyme can be recycled several times before it is removed from the system, thereby minimizing the cost of this reagent. Preferably better separation of liquid and solids is obtained if the supernatant is separated from the insoluble collagen by centrifugation.

EXAMPLE 4

An experiment was conducted in which 750 ml whitewater (recycle water from a papermaking process) was substituted for the tap water in the standard recipe of Example 3 above. Then 15.5 g Teepak collagen were added, the pH was adjusted to 2.14 with 40 drops of concentrated HCl, and 0.375 g of pepsin were added. Because the room temperature was elevated during this experiment, the reaction was conducted at 29°–31° C., and the solubilization appeared to proceed more quickly than standard reactions at 25°–26° C. In this single reaction, good viscosity was developed, the solids were nearly completely solubilized, and there appeared to be no problem with conducting the process in this solution (see the Table). Recycling whitewater from a papermaking process in this way will greatly diminish the amount of water introduced to the process.

TABLE

SOLUBILIZED HIGH-MOLECULAR-WEIGHT COLLAGEN MADE IN WHITEWATER FROM PAPER MAKING

| Time (hours) | Viscosity 20 rpm | Viscosity 100 rpm | Viscosity Ratio |
|---|---|---|---|
| 0 | — | — | — |
| 18.5 | 415 | 177 | 2.34 |
| 22 | 440 | 186 | 2.37 |
| 26.7 | 365 | 166 | 2.20 |
| 42 | 280 | 136 | 2.06 |

EXAMPLE 5

In this example, 500 gal of Savannah, Ga. tap water was delivered to a double-paddle, 600 gal. stainless steel tank, and 75# of Teepak collagen (13.5# solids @ 18% solids) was dispersed in the water. Approximately 1.4 liters of concentrated HCl was added to bring the pH to 2.14. Pepsin (1.01 kg; Sigma Lot #70H0437) was slowly added, then the tank was covered with polyethylene film and the tank was stirred overnight. After approximately 20 hours, hydrolysis was incomplete (viscosity ratio=1.32). Because the liquid and room temperatures were relatively low (approximately 20° C.), it was decided to attempt to raise the liquid temperature by putting live steam onto the outside bottom of the tank. The steam was used for about 2.5 hours, by which time the liquid temperature was 23° C., the viscosity ratio was 2.15, and the steam heating was discontinued.

Figure 4:
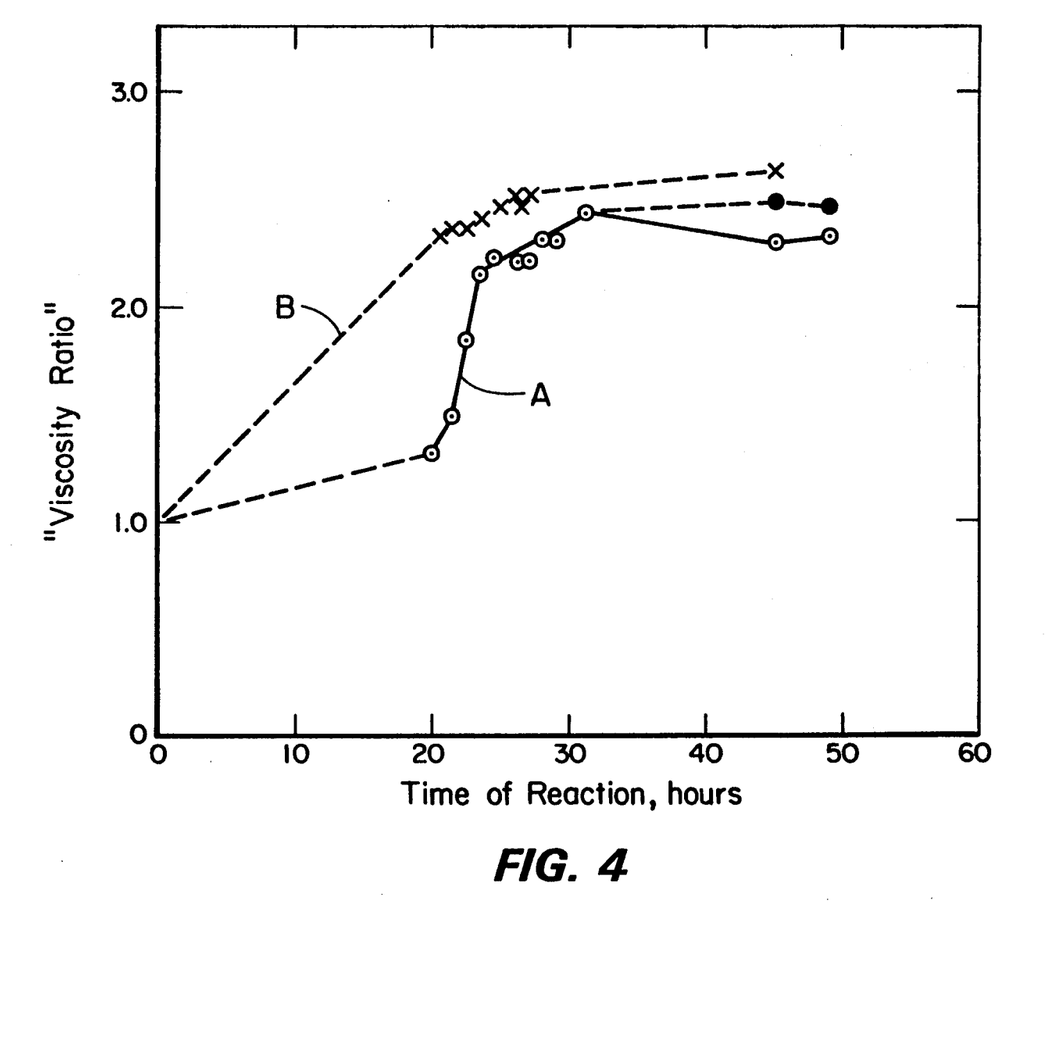
FIG. 4 is a plot of the development of viscosity ratios in Examples 5 (denoted by A) and 6 (denoted by B).

At approximately 31 hours, the viscosity ratio was 2.43, which is relatively high for this reaction. It was decided to adjust the pH in the tank to approximately 3.0, by the addition of approximately 450 grams of NAOH flakes, in order to stabilize the solution (slow/stop the pepsin reaction) for use in paper the next day. Approximately 55 gal of the pH=2.1 solution were saved in 5-gal containers prior to the pH adjustment. Because the viscosity ratio dropped slightly overnight for the pH=2.1 solution (open circles, (-⊙-)

,in FIG. 4 and denoted by A) compared to the pH=3.0 solution (closed circles, {-●-}

, it is concluded that pH adjustment is helpful in maintaining the highest possible molecular weight in the product during storage at room temperature.

After approximately 24 hours of reaction, some floating solid material (presumed to be fat because of its low density) was observed on the upper surface of the collagen solution near the mixer shaft. Although no attempt was made in this experiment to remove this residue, it can be easily skimmed from the preparation if the residual fat was found to be detrimental to collagen performance.

Prior to using the collagen solution made in this example and in Example 6, described below, the solution was filtered by passing it through a knitted plastic screen with openings approximately 1×3 mm, in order to remove a small number of very slowly degrading skin particles. These particles are characteristically the last material to be dissolved by pepsin and can often be found in the 3-5 mm size range. A large sample of these residual particles and their dry weight was measured. Based on projecting this sample to the entire batch of collagen solution, it was estimated that more than 95% of the initial solids were solubilized in this process.

EXAMPLE 6

In this example, the same tank was filled with 500 gal of Savannah, Ga. tap water, which in January was very cold—about 11° C. Teepak collagen (79.5#; 12.5# of solids at 15.67% dry wt.) was dispersed in this water, then 1.5 liters of concentrated HCl was added to bring the pH to 2.18. Pepsin (1.01 kg; Sigma Lot #70H0437) was slowly added, then the tank was covered with polyethylene film. Live steam was placed on the outer bottom of the tank for approximately 4 hours to raise the liquid temperature from 11.5° to 25° C. At this time the pH was 2.40; an additional 0.4 liters of concentrated HCl was added to bring the pH down to 2.29. The tank was draped with polyethylene film to insulate the tank overnight. After approximately 28 hours the viscosity ratio was 2.51, with the temperature at about 22° C. at pH=2.46. Approximately 600 g of flaked NaOH was added to bring the tank contents to pH=2.98, the tank was covered as before and stirred overnight. The final viscosity ratio was 2.61. Results are shown in FIG. 4 at B (-x-).

Since the collagen solution in Example 6 was produced at about a 2°-3° C. higher reaction temperature during the first day than that in Example 5, the reaction appears to have progressed more rapidly, reaching completion about 4-5 hours sooner. When the pH was adjusted to about 3.0 the final solution appears to have slowed the enzymatic reaction so that little degradation of the soluble product was observed overnight.

The process is intended to produce nearly complete conversion of beef hides to a collagen solution using an enzymatic hydrolysis reaction. Objectives for the process are production of the highest possible molecular weight soluble product at the maximum yield, while conversion costs and fixed capital expenditures are minimized. The process is not intended to produce food- or medical-grade soluble collagen, and therefore requirements for production of clean solutions are minimal, and no purification of the soluble collagen is anticipated. No attempt has been made to remove the remnants of the other skin components (fat, proteoglycans, other proteins, salts, etc.), which are present in the ground-split feedstock at concentrations lower than collagen.

The process will require a series of cutters and grinders to reduce the feedstock limed splits to a shredded material that can be readily converted to soluble collagen. As cited above, the "front end" of the process will likely look similar to the USDA process for producing comminuted collagen. Depending on the pretreatment of the hides employed to prevent microbial growth, the hides may need to be delimed or acidified to remove residual calcium salts or other biocides. The ground solids are then mixed with process water (perhaps a reduced-solids whitewater stream from a paper plant), the pH is titrated to 2.0-2.2, and enzyme is added to begin the solubilization process. Following conversion, the soluble solids can be pumped directly to a paper making process and mixed with refined pulp solids or stabilized and stored.

In small-scale tests, maximum interaction between collagen and pulp solids appears to result if the pH of the solution is about 4.0 or less and the pulp consistency is 1.0% or lower. Therefore, adjustment of the pulp in the holding tank to about pH 4.0 or less appears to be beneficial.

Collagen solutions prepared by this process appear to be stable at room temperature for 12-24 hours, and stability can be enhanced by increasing solution pH to 3.0-3.5 and/or by reducing the solution temperature to 5°-10° C.

The process has demonstrated the feasibility of production of a low-cost high-molecular-weight soluble collagen product by the substantially complete solubilization of beef hide collagen (ground limed-splits). The process can be conducted at near-ambient conditions and is relatively easy to control.

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit of the scope of the invention.

I claim:

1. A method for producing an aqueous solution of high molecular weight solubilized collagen comprising:
   a. providing an aqueous ground slurry of insoluble collagen;
   b. adjusting the water or solid content of said wet ground slurry whereby said insoluble collagen is at a concentration that promotes substantially maximum solubilized collagen concentration and molecular weight in a final product;
   c. adjusting the pH of said slurry from Step b to obtain activity for a proteolytic enzyme added in Step d;
   d. adding said proteolytic enzyme to said pH adjusted slurry and reacting at a temperature, T, and for a time, t, effective for forming a solution of high molecular weight solubilized collagen from said insoluble collagen particles;
   e. controlling said reaction to obtain a high concentration of soluble collagen and a high molecular weight of said solubilized collagen by simultaneously measuring the concentration of solubilized collagen and the molecular weight of said solubilized collagen, whereby said reaction is complete when said molecular weight and said concentration are substantially maximized;

f. adding additional water and insoluble collagen to said solution containing high molecular weight solubilized collagen in Step d and mixing;

g. separating at least some of the solution containing high molecular weight solubilized collagen from the insoluble collagen and returning the insoluble collagen to Step b, whereby at least a portion of the proteolytic enzyme is recycled, and the separated solution containing high molecular weight solubilized collagen is withdrawn as product.

2. The method of claim 1, further comprising repeating Steps f and g one or more times.

3. The method of claim 1, comprising stopping said reaction by
   (1) adjusting said pH to that where said proteolytic enzyme is substantially inactive; and/or
   (2) reducing the temperature to that where said proteolytic enzyme is substantially inactive.

4. The method of claim 1, comprising controlling said reaction by measuring solution viscosity at two different shear rates whereby said reaction is complete when a ratio of, (viscosity at low shear)/(viscosity at high shear) is substantially maximized.

5. The method of claim 1, further comprising said viscosity ratio is at least 75% of maximum.

6. The method of claim 1, further comprising in Step b, adjusting said liquid or solids content of said wet ground slurry so that said solids are adjusted to a concentration of about 0.1 to about 1.0 wt %.

7. The method of claim 1, whereby said temperature, T, comprises about 5° C. to about 35° C.

8. The method of claim 1, whereby said temperature, T, comprises about 15° C. to about 30° C.

9. The method of claim 1, whereby, in Step b, said solids concentration is between about 0.3 to 0.35 wt %; and in Step e. controlling said reaction at a temperature of about 20° to about 30° C., and for time of 24 to 48 hours.

10. The method of claim 1, further comprising: selecting the proteolytic enzyme from the group consisting of porcine mucosal pepsin, bromelain, chymopapain, chymotrypsin, collagenase, ficin, papain, peptidase, proteinase A, proteinase K, trypsin, and combinations of such enzymes.

11. The method of claim 10, further comprising: adjusting the pH to about 1.5-3.0 and the temperature to between about 26° to about 28° C., when porcine mucosal pepsin is selected.

12. The method of claim 1, further comprising: whereby at least 80 wt % of said insoluble collagen is converted to soluble collagen and the number average molecular weight is above 300,000 daltons.

13. The method of claim 12, further comprising: whereby at least 80 wt % of said insoluble collagen is converted to soluble collagen and the number average molecular weight is above 600,000 daltons.

14. The method of claim 1, further comprising: whereby at least 90 wt % of said insoluble collagen is converted to soluble collagen and the number average molecular weight is above 1,000,000 daltons.

* * * * *